United States Patent
Higashiyama et al.

(10) Patent No.: US 9,610,262 B2
(45) Date of Patent: Apr. 4, 2017

(54) THERAPEUTIC AND/OR PREVENTIVE AGENT COMPRISING 1-INDANSULFAMIDE DERIVATIVE FOR PAIN

(71) Applicant: Eisai R&D Management Co., Ltd., Tokyo (JP)

(72) Inventors: Hiroyuki Higashiyama, Tsukuba (JP); Yuji Kazuta, Tsukuba (JP); Keisuke Hashimoto, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/102,046

(22) PCT Filed: Dec. 17, 2014

(86) PCT No.: PCT/JP2014/083374
§ 371 (c)(1),
(2) Date: Jun. 6, 2016

(87) PCT Pub. No.: WO2015/093515
PCT Pub. Date: Jun. 25, 2015

(65) Prior Publication Data
US 2016/0303058 A1    Oct. 20, 2016

(30) Foreign Application Priority Data

Dec. 19, 2013   (JP) ................................ 2013-262743

(51) Int. Cl.
*A61K 31/165*   (2006.01)
*A61K 31/18*    (2006.01)

(52) U.S. Cl.
CPC ............ *A61K 31/165* (2013.01); *A61K 31/18* (2013.01)

(58) Field of Classification Search
CPC ............................. A61K 31/165; A61K 31/18
See application file for complete search history.

(56) References Cited

FOREIGN PATENT DOCUMENTS

| WO | WO 2007/075752 | 7/2007 |
| WO | WO 2007/095615 | 8/2007 |
| WO | WO 2010/115952 | 10/2010 |
| WO | WO 2012/038081 | 3/2012 |
| WO | WO 2013/191144 | 12/2013 |

OTHER PUBLICATIONS

Breivik et al., "Survey of chronic pain in Europe: Prevalence, impact on daily life, and treatment," Eur J Pain, 10(4):287-333, May 2006.

Dubuisson and Dennis, "The formalin test: A quantitative study of the analgesic effects of morphine, meperidine, and brain stem stimulation in rats and cats," Pain, 4:161-174, Oct. 1977-Apr. 1978.

International Preliminary Report on Patentability and Written Opinion in Application No. PCT/JP2014/083374, dated Jun. 30, 2016, 6 pages.

(Continued)

*Primary Examiner* — Savitha Rao
*Assistant Examiner* — Angela Brown-Pettigrew
(74) *Attorney, Agent, or Firm* — Fish & Richardson P.C.

(57) ABSTRACT

The present invention is directed to a method of treating pain comprising the administering the following 1-indansulfamide compounds: N-[(1S)-2,2,5,7-tetrafluoro-2,3-dihydro-1H-inden-1-yl]sulfamide, (−)-N-(7-chloro-2,2,5-trifluoro-2,3-dihydro-1H-inden-1-yl)sulfamide, N-[(1S)-2,2-difluoro-7-methyl-2,3-dihydro-1H-inden-1-yl]sulfamide, and N-[(1S)-2,2,5-trifluoro-7-methyl-2,3-dihydro-1H-inden-1-yl]sulfamide.

12 Claims, 2 Drawing Sheets

(56) References Cited

OTHER PUBLICATIONS

International Search Report in Application No. PCT/JP2014/083374, dated Jan. 27, 2015, 2 pages.
Merskey et al., "Pain terms: A list with definitions and notes on usage," Pain, 6(3):247-252, 1979.
Phillips, "JCAHO Pain management standards are unveiled," J Am Med Assoc, 284(4):428-429, Jul. 26, 2000.
Terai et al, "Japanese Translation of Neuropathic Pain—Report of Committee on Terminology of Japan Society of Pain Clinicians," Journal of Japan Society of Pain Clinicians, Report of Term Committee, 16(4):509-514, 2009.
Treede et al., "Neuropathic pain: Redefinition and a grading system for clinical and research purposes," Am Acad Neur 70:1630-1635, Apr. 29, 2008.
Wang and Wang, "Animal and cellular models of chronic pain," Advanced Drug Delivery Reviews, 55(8):949-965, Aug. 15, 2003.
Wu and Raja, "Treatment of acute postoperative pain," Lancet, 377:2215-2225, Jun. 25, 2011.

* P < 0.05,  P < 0.01, * P < 0.001 vs Vehicle
(Holm-Sidak's multiple comparisons test)

GBP : Gabapentin

* P < 0.05,  P < 0.01, * < 0.001 vs Vehicle
(Holm-Sidak's multiple comparisons test)

THERAPEUTIC AND/OR PREVENTIVE AGENT COMPRISING 1-INDANSULFAMIDE DERIVATIVE FOR PAIN

TECHNICAL FIELD

The present invention relates to a therapeutic and/or prophylactic agent for pain comprising a 1-indanesulfamide derivative, a salt thereof or a prodrug thereof.

BACKGROUND ART

According to Classification of International Association for the Study of Pain (IASP), "pain" is defined as "An unpleasant sensory and emotional experience associated with actual or potential tissue damage; or described in terms of such damage" (Non Patent Literature 1).

Pain is generally classified as being acute or chronic. Acute pain is pain that has been present for not more than three months. Acute pain begins suddenly and is sharp in quality in most cases. Acute pain may be caused by many events or circumstances, such as surgery, broken bones, dental treatment, burns or cut, etc. Chronic pain is pain lasting for not less than three months. Common chronic pain includes headache, low back pain, cancer pain, arthritis pain, neuropathic pain, psychogenic pain (pain occurring in the absence of physical cause of pain, such as past disease or injury). Neuropathic pain, which has also been translated into neurogenic pain, is refractory pain resulting from damages or diseases to the peripheral or central somatic sensory nerve system, including diabetic neuropathy, trigeminal neuralgia, and postherpetic neuralgia (Non Patent Literatures 2 and 3).

Pain is a common medical problem, and relief of pain is an important therapeutic goal. Pain is most commonly treated with analgesics. Analgesics are roughly divided into three categories: (1) opioid analgesics; (2) nonopioid analgesics, such as anti-inflammatory steroids, acetaminophen, and dipyrone; and (3) "adjuvant analgesics" (a diverse group of drugs which are known as "drugs that do not have an analgesic action as a primary pharmacological action but may enhance an analgesic effect when used in combination with analgesics and show an analgesic effect in selected circumstances").

While opioid analgesics provide a strong analgesic effect by acting on the opioid receptor in the central nervous system; their use is limited because of their serious adverse drug reactions and dependency. Although nonopioid analgesics have an analgesic effect, the effect is weak and various adverse drug reactions may be induced. In addition, no therapeutic drug effective for chronic pain such as neuropathic pain associated with diabetic neuropathy, trigeminal neuropathy and herpes zoster has yet been found, and the development of a drug effective for a broad range of pain, including acute pain and chronic pain, has been desired.

Although a variety of analgesics are currently available for the treatment of pain, huge unmet medical needs still exist in pain treatment. Recent reports estimate that an adequate analgesic effect on acute pain is realized only in one of four patient undergoing surgical treatment (Non Patent Literatures 4 and 5). In addition, inadequate treatment of acute pain may lead to a variety of symptoms, including anxiety, depression, insomnia, fatigue, decreased appetite, nausea and vomiting. Further, unrelieved acute pain may progress to chronic pain.

On the other hand, as concerning chronic pain, WHO estimates that 20% of population of the world has some degree of chronic pain. Chronic pain has a significant impact on both direct health-care costs and associated indirect costs (for example, disability payments, lost productivity). Because adequate relief cannot be achieved in approximately 40% of patients with chronic pain, chronic pain is now considered to be a significant public health problem (Non Patent Literature 6).

Effective treatment for acute pain and chronic pain still remains an unmet medical need of many patients. Therefore, it has been strongly desired to develop a therapeutic agent effective for acute pain and chronic pain.

As animal models of acute pain, models for evaluating transient pain, such as tail-flick test, a flinch/jump test, a hot-plate test, a pinch test are known. As a model for acute persistent pain, a formalin test is used. (Non Patent Literature 7)

On the other hand, as models of chronic pain, a rat chronic constriction injury model (CCI model) and the like are known. Classified by the cause of pain, the CCI model is considered to be a disease model corresponding to neuropathic pain. (Non Patent Literature 8)

As sulfamide derivatives having an analgesic effect, low molecular compounds disclosed in Patent Literatures 1 and 2 are known. 1-Indanesulfamide derivatives with an analgesic effect have not been known, however.

CITATION LIST

Patent Literature

Patent Literature 1: WO2007/095615
Patent Literature 2: WO2007/075752

Non Patent Literature

Non Patent Literature 1: International Association for the Study of Pain (1979), "Pain Definitions", Pain 6(3): 247-248

Non Patent Literature 2: "Japanese translation of Neuropathic Pain—A report of Terminology Committee, the Japan Society of Pain Clinicians", Journal of Japan Society of Pain Clinicians (2009), 16(4) 509-514

Non Patent Literature 3: Treede, R. D., Jensen, T. S., Campbell, J. N., et al., (2008), "Neuropathic pain: Redefinition and a grading system for clinical and research purposes", Neurology 70: 1630-1635

Non Patent Literature 4: Phillip, D. M. (2000), "JCAHO: Pain management standards are unveiled", JAMA 284(4): 428-429

Non Patent Literature 5: Wu, C. L. and Raja, S. N. (2011), "Treatment of acute postoperative pain", Lancet 377(9784): 2215-2225

Non Patent Literature 6: Breivik, H., Collett, B., Ventafridda, V, Cohen, R. and Gallacher, D. (2006), "Survey of chronic pain in Europe: Prevalence, impact on daily life, and treatment", European Journal of Pain 10 (4): 287-333

Non Patent Literature 7: Dubuisson, D. and Stephen, G. (1977), "The formalin test: A quantitative study of the analgesic effects of morphine, meperidine, and brain stem stimulation in rats and cats", Pain 4(2): 161-174

Non Patent Literature 8: Wang, L. X. and Wang, Z. (2003), "Animal and cellular models of chronic pain" Advanced Drug Delivery Reviews 55(8): 949-965

SUMMARY OF INVENTION

Technical Problem

An object of the present invention is to provide a therapeutic and/or prophylactic agent for pain, which exhibits an analgesic effect in various animal models and may be applicable to various types of pain.

Solution to Problem

The present inventors conducted studies using the mice hot plate test to confirm an analgesic effect on acute pain and using the rat chronic constriction injury (CCI) model to confirm an analgesic effect on chronic pain, respectively.

As the results of the study using the mice hot plate test, the inventors have found out that 1-indanesulfamide derivatives have an inhibitory effect on acute pain induced by nociceptive stimulus. In addition, as the results of the study using the rat chronic constriction injury (CCI) model, the inventors have found out that 1-indanesulfamide derivatives have an inhibitory effect on chronic pain caused by nerve ligation. The inventors have thus accomplished the present invention.

Specifically, the present invention relates to:
[1] A therapeutic and/or prophylactic agent for pain comprising a compound selected from the following group:
  (1) N-[(1S)-2,2,5,7-tetrafluoro-2,3-dihydro-1H-inden-1-yl]sulfamide,
  (2) (−)-N-(7-chloro-2,2,5-trifluoro-2,3-dihydro-1H-inden-1-yl)sulfamide,
  (3) N-[(1S)-2,2-difluoro-7-methyl-2,3-dihydro-1H-inden-1-yl]sulfamide, and
  (4) N-[(1S)-2,2,5-trifluoro-7-methyl-2,3-dihydro-1H-inden-1-yl]sulfamide,
  or a pharmaceutically acceptable salt thereof;
[2] The therapeutic and/or prophylactic agent according to [1], wherein the pain is acute pain or chronic pain;
[3] The therapeutic and/or prophylactic agent for pain according to [1], wherein the pain is neuropathic pain;
[4] The therapeutic and/or prophylactic agent for pain according to [1], wherein the pain is diabetic neuropathy, trigeminal neuropathy or postherpetic neuralgia;
[5] The therapeutic and/or prophylactic agent for pain according to any one of [1] to [4], wherein the agent is administered orally, sublingually, intranasally, rectally, intragingivally, intravenously, intramuscularly, intra-articularly, subcutaneously, inhalationally, transdermally or epidurally; and
[6] The therapeutic and/or prophylactic agent for pain according to any one of [1] to [4], wherein the agent is administered orally, sublingually, intravenously, intramuscularly, intia-articularly, subcutaneously, transdermally or epidurally.

Advantageous Effects of Invention

The agent according to the present invention has an inhibitory effect on acute pain induced by nociceptive stimuli in the mice hot plate test and on chronic pain caused by nerve ligation in the rat CCI model. In addition, the agent according to the present invention exhibits an analgesic effect in the mice formalin test which is an animal model of acute persistent pain. The agent of the present invention can thus be used as a therapeutic agent and/or prophylactic agent for acute pain and chronic pain.

DESCRIPTION OF EMBODIMENTS

Figure 1:
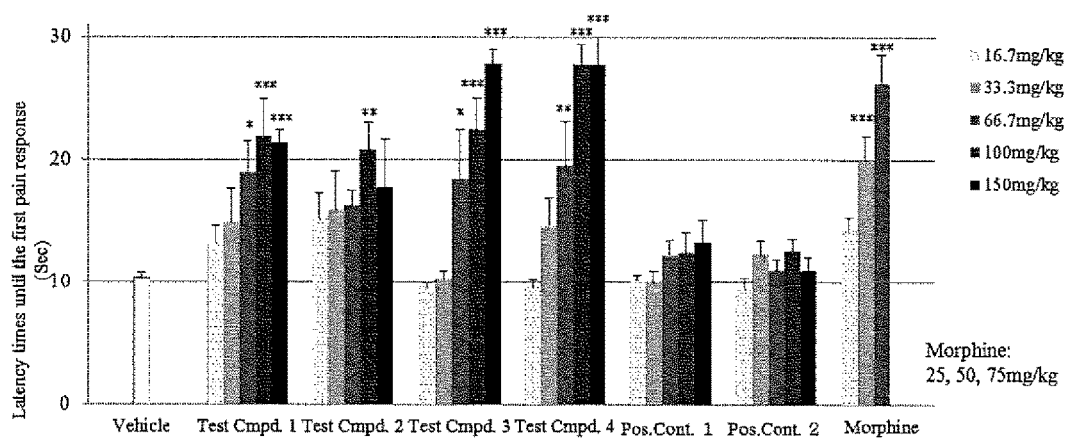
FIG. 1 is a graph showing the results of Test Example 1 in which Test Compounds 1, 2, 3 and 4 are administered.

The present invention is described in detail in the following.

Although the 1-indanesulfamide compound used in the invention may have crystal polymorphs, the compound is not limited to any one of the polymorphs and may be present as a single crystal form or a mixture of single crystal forms. And amorphous form is also included.
In addition, the compound may form pharmaceutically acceptable salts and various solvates.

Hereinafter, the meanings of terms, symbols and the like described in the present specification are explained.

The "pharmaceutically acceptable salt" in the present specification is not particularly limited insofar as it forms a salt with the compound and is pharmaceutically acceptable.

A solvate means a state where a solvent used in reaction or crystallization is incorporated in crystal, without forming a covalent bond with the molecule or ion of the compound. Examples of a solvate are hydrate, alcoholate (ethanolate) and the like.

Starting material compounds, intermediates and various reagents in the production of the compound used in the invention may form salts or solvates, all vary depending on the starting material, the solvent used or the like, and are not particularly limited insofar as they do not inhibit the reaction. Also, needless to say, the solvent used varies depending on the starting material, the reagent or the like, and is not particularly limited insofar as it does not inhibit the reaction and dissolves the starting material to a certain extent. When the compounds are obtained as free forms, they can be converted to acceptable salts or solvates by conventional methods.

Various isomers of the compounds or the intermediates of the present invention (such as geometric isomers, optical isomers, rotamers, stereoisomers, tautomers and the like) can be purified and isolated using common separation methods, for example, recrystallization, diastereomeric salt formation, enzymatic resolution and various chromatography methods (such as thin layer chromatography, column chromatography and gas chromatography).

The compounds or pharmaceutically acceptable salts thereof used in the present invention can be formulated by conventional methods, and examples of dosage forms include oral formulations (such as tablets, granules, powders, capsules and syrups), sublingual tablets, injections (for intravenous administration, intramuscular administration, subcutaneous administration, intraperitoneal administration, intra-articular administration, or epidural administration) and external preparations (such as transdermal absorption formulations (such as ointments and patches), nasal preparations, suppositories and the like).

The solid formulations such as tablets, capsules, granules and powders may contain usually 0.001 to 99.5 wt %, preferably 0.01 to 90 wt % or the like, of the compounds or pharmaceutically acceptable salts thereof used in the present invention.

When oral solid formulations are manufactured, tablets, granules, powders and capsules can be prepared by adding diluents, binders, disintegrants, lubricants, colorants and the like to the compounds or pharmaceutically acceptable salts thereof used in the present invention as necessary and treating by conventional methods. These formulations may also be film coated as necessary.

Examples of diluents include lactose, corn starch and microcrystalline cellulose, examples of binders include hydroxypropylcellulose and hydroxypropylmethylcellulose, and examples of disintegrants include carboxymethylcellulose calcium and croscarmellose sodium.

Examples of lubricants include magnesium stearate and calcium stearate, and examples of colorants include titanium oxide.

Examples of film coating agents include hydroxypropylcellulose, hydroxypropylmethylcellulose and methylcellulose.

There is, of course, no limitation to the excipients mentioned above.

For production of an injection (for intravenous administration, intramuscular administration, subcutaneous administration, intraperitoneal administration, intra-articular administration or epidural administration), a pH regulator, buffering agent, suspending agent, emulsifiers, solubilizing agents, antioxidant, preservative (antiseptic agent), isotonizing agent or the like may be added to the compound or pharmaceutically acceptable salts thereof as the case requires, and production carried out by an ordinary method. It may also be freeze-dried as a freeze-dried preparation to be dissolved at the time of use. Such injections can be administered into vein, under the skin, or into the muscle, for example.

Examples of pH regulators and buffering agents include organic acids or inorganic acids and/or salts thereof, examples of suspending agents include methylcellulose, polysorbate 80 and carboxymethylcellulose sodium, examples of emulsifiers include polyoxyethylene castor oil, hydroxypropylcellulose and lecithin, examples of solubilizing agents include polysorbate 80 and polyoxyethylene sorbitan monolaurate, examples of antioxidants include α-tocopherol, examples of preservatives include methyl parahydroxybenzoate and ethyl parahydroxybenzoate, and examples of isotonizing agents include glucose, sodium chloride and mannitol, naturally with no particularly limitation to these.

Such injections may contain usually 0.00001 to 99.5 wt %, preferably 0.0001 to 90 wt % of the compounds or pharmaceutically acceptable salts thereof used in the invention.

For production of an external preparation, a base starting material may be added to the compound of the present invention or a pharmaceutically acceptable salt thereof, and if necessary any of the aforementioned emulsifiers, preservatives, pH regulators or colorants added to produce, for example, a transdermal absorption preparation (ointment, medical patch or the like), nasal drops or suppository, by an ordinary method.

Conventionally used various raw materials for pharmaceuticals, quasi drugs, cosmetics and the like can be used as base materials, and examples include raw materials such as animal and vegetable oils, mineral oils, ester oils, waxes, higher alcohols and purified water.

Such external preparations may contain usually 0.00001 to 99.5 wt %, preferably 0.0001 to 90 wt % of the compounds or pharmaceutically acceptable salts thereof used in the invention.

A dosage of the medicine according to the present invention typically varies depending on the symptom, age, sex, weight or the like, but is acceptable if it is a dosage sufficient to exhibit a desired effect. For example, for an adult, a dosage of about 0.1 to 5000 mg (preferably 0.5 to 1000 mg, more preferably 1 to 600 mg) per day is used in one dose during one or more days or in 2 to 6 divided doses for one day.

EXAMPLES

The Compounds used in the invention can be produced by the methods described in production examples below, for example, and the effects of the compounds can be confirmed by the methods described in test examples below. However, these methods are illustrative and may be changed without departing from the scope of the present invention and the present invention is not limited to the following specific examples in any case.

Compounds, to which publication names or the like are attached, were produced in accordance with the publications or the like.

All of the abbreviations used in this description are conventional ones known to those skilled in the art. The following abbreviations are used in the following examples.
BAST: bis(2-methoxyethyl)aminosulfur trifluoride
Bn: benzyl
Boc: tert-butoxycarbonyl
DCM: dichloromethane
DMF: N,N-dimethylformamide
DMSO: dimethylsulfoxide
$^1$H-NMR: proton Nuclear Magnetic Resonance spectrometry
HPLC: High Performance Liquid Chromatography
I.D.: Internal Diameter
LC-MS: liquid chromatography-mass spectrometry
m-: meta-
n-: normal-
NBS: N-bromosuccinimide
o-: ortho-
p-: para-
PPTS: pyridinium p-toluenesulfonate
Selectfluor™:
N-fluoro-N'-chloromethyl-triethylenediamine-bis(tetrafluoroborate)
t-: tertiary-
TBS: tert-butyldimethylsilyl
TEA: triethylamine
THF: tetrahydrofuran
THP: tetrahydropyran
Z(Cbz): benzyloxycarbonyl The "room temperature" in the following preparation examples typically refers to about 10° C. to about 35° C. "%" indicates wt % unless otherwise specified. The ratio of the solvents in silica gel chromatography, however, shows the volume ratio of the solvents to be admixed.

Chemical shifts in proton nuclear magnetic resonance spectra are recorded in δ units (ppm) relative to tetramethylsilane and coupling constants are recorded in Hertz (Hz). Patterns are designated as s: singlet, d: doublet, t; triplet, q: quartet, m: multiplet, brs; broad singlet Optical resolution of the compounds performed by GILSON HPLC system (Pump; Master Pump Model 305, Slave Pump Model 306, Pumphead 50SC, Dynamic mixer Model 811D/A, Manometric Module Model 806, UV detector; UV/VIS detector Model 155, Injector, Fraction collector; Model 215, Column; Selected from DAICEL CHIRALPAK® AD-H, IA, IB, IC, ID, IE, IF, DAICEL CHIRALCEL®, OD-H, OJ-H, 20 mm I.D.×250 mm). After detection of fractions by the UV detector, optical rotation (+/−) was measured using the optical rotation detector (OR-2090, JASCO, mercury-xenon (Hg—Xe) lamp, 150 W).

With respect to chromatography, if there is described a silica gel column chromatography, YAMAZEN parallel prep (column: YAMAZEN Hi-Flash™ Column (Silicagel), size; S (16×60 mm), M (20×75 mm), L (26×100 mm), 2 L (26×150 mm) or 3 L (46×130 mm)), spherical silica gel for chromatography PSQ 60B™ of FUJI SILYSIA CHEMICAL CO., LTD., silica gel for chromatography BW-300™ of Fuji Silysia Chemical. Co., Ltd., Wakogel® C-200 (Wako Pure Chemical Industries, Ltd.), or silicagel 60 (70-230 mesh) of Merck Ltd. Japan was used.

Also, if there is a description with NH silica gel column chromatography, YAMAZEN parallel prep (column: YAMAZEN Hi-Flash™ Column (Amino), size; S (16×60 mm), M (20×75 mm), L (26×100 mm), 2 L (26×150 mm) or 3 L (46×130 mm)) or NH SILICA GEL (200-350 mesh) of FUJI SILYSIA CHEMICAL CO., LTD. was used.

In the nomenclature of compounds in the present specification, (+)-, (−)-, (R) and (S) represent (+), (−), (R) and (S) configurations of the enantiomers, respectively. And "*" in the steric configuration shows the relative configuration, and unless specifically indicated, it means a certain enantiomer.

Production Example 1

Synthesis of N-[(1S)-2,2,5,7-tetrafluoro-2,3-dihydro-1H-inden-1-yl]sulfamide

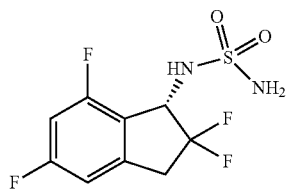 [SMILES: NS(=O)(=O)N[C@H]1c2c(F)cc(F)cc2CC1(F)F]

(1) Synthesis of 2,5,7-trifluoro-2,3-dihydro-1H-inden-1-one

Selectfluor™ (1.16 g, 3.27 mmol) was added to a solution of 5,7-difluoro-1-indanone (CAS No. 84315-25-3, 500 mg, 2.97 mmol) in MeOH (20 mL) at room temperature. The mixture was refluxed for 2 hours and cooled to room temperature. Then the solvent was distilled off under reduced pressure. The residue was treated with DCM and the insoluble matter was filtered off. Then the solvent was distilled off under reduced pressure. The residue was dissolved in MeCN (10 mL) and 5 N HCl (5 mL). The solution was stirred at room temperature for 1 hour, and then concentrated in vacuo. The residue was partitioned between AcOEt and H2O. The organic layer was washed with brine, dried over MgSO$_4$, and filtrated. The solvent was concentrated in vacuo to afford the title compound (547 mg, 2.94 mmol).

$^1$H-NMR (400 MHz, CDCl$_3$): δ ppm 3.11-3.36 (m, 1H) 3.49-3.77 (m, 1H) 5.10-5.40 (m, 1H) 6.82 (td, J=9.0, 1.9 Hz, 1H) 6.90-7.04 (m, 1H).

(2) Synthesis of 2,2,5,7-tetrafluoro-2,3-dihydro-1H-inden-1-one

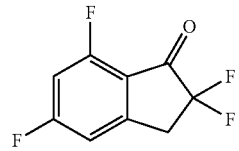 [SMILES: O=C1c2c(F)cc(F)cc2CC1(F)F]

t-Butyldimethylsilyl trifluoromethanesulfonate (1.00 mL, 4.35 mmol) was added to a solution of the product obtained in Production example 1-(1) (540 mg, 2.90 mmol) and TEA (1.21 mL, 8.70 mmol) in DCM (20 mL) at 0° C. The mixture was stirred at room temperature for 5 hours. Then to the reaction mixture were added diethyl ether and saturated aqueous Na$_2$CO$_3$ and the layers were separated. The organic layer was successively washed with 1N HCl, saturated aqueous Na$_2$CO$_3$, and brine, and dried over Na$_2$SO$_4$. The solvent was evaporated in vacuo and the residue was dried under reduced pressure.

The residue was dissolved in MeCN (20 mL), and Selectfluor™ (1.13 g, 3.19 mmol) was added at room temperature. After stirring the mixture at the same temperature for 11 hours, the solvent was distilled off under reduced pressure. The residue was dissolved in DCM and insoluble matter was filtered off. The filtrate was concentrated in vacuo. The residue was purified by flash column chromatography (Yamazen HI-FLASH™ column Silicagel L size, 20 mL/min, gradient 10% to 50% AcOEt in n-heptane) to afford the title compound as white solids (532 mg, 2.61 mmol).

$^1$H-NMR (400 MHz, CDCl$_3$): δ (ppm) 3.57 (t, J=12.4 Hz, 2H) 6.74-6.94 (m, 1H) 6.95-7.08 (m, 1H).

(3) Synthesis of 2,2,5,7-tetrafluoro-2,3-dihydro-1H-inden-1-amine

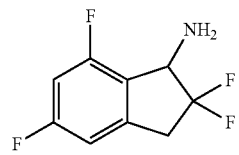 [SMILES: NC1c2c(F)cc(F)cc2CC1(F)F]

Ammonium acetate (427 g, 55.4 mmol) was added to a solution of the product obtained in Production example 1-(2) (377 mg, 1.85 mmol) in isopropanol (16 mL) at room temperature and the mixture was refluxed for 30 min. Sodium cyanoborohydride (348 mg, 5.54 mmol) was added to the reaction mixture and stirred under reflux for 7 hours. After cooling to room temperature, AcOEt and 2N NaOH were added to the reaction mixture, and the layers were separated. The organic layer was concentrated in vacuo. Water was added to the residue, and partitioned between AcOEt and 1N HCl. The aqueous layer was basified with 2N NaOH and extracted with AcOEt. The organic layer was dried over Na2SO4, evaporated and dried to afford the title compound (210 mg, 1.02 mmol).

ESI-MS; m/z 206 [M+H]$^+$.

¹H NMR (400 MHz, CDCl₃): δ (ppm) 3.26-3.55 (m, 2H) 4.59 (dd, J=13.3, 5.3 Hz, 1H) 6.61-6.86 (m, 2H).

(4) Synthesis of benzyl N-(2,2,5,7-tetrafluoro-2,3-dihydro-1H-inden-1-yl)sulfamoylcarbamate

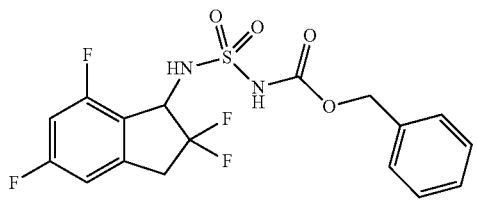 [SMILES: O=C(NS(=O)(=O)NC1c2c(F)cc(F)cc2CC1(F)F)OCc1ccccc1]

To a DCM solution (10 mL) of the product obtained in Production example 1-(3) (200 mg, 0.975 mmol), [(Benzyloxy)carbonyl]{[4-(dimethyliminio)pyridin-1(4H)-yl]sulfonyl}amide (CAS No. 1037211-09-8, 654 mg, 1.95 mmol, prepared according to the method described in WO2008083248) and TEA (0.55 mL, 3.90 mmol) were added at room temperature. The resulting solution was stirred for 24 hours under reflux. After cooling to room temperature, AcOEt and 1N HCl was added to the reaction mixture. The layers were separated, and the organic layer was dried over MgSO₄ and evaporated in vacuo. The residue was purified by column chromatography (Silicagel, 30% AcOEt in n-heptane) to afford the title compound as white solids (316 mg, 0.755 mmol).

ESI-MS; m/z 441 [M+Na]⁺.

¹H-NMR (400 MHz, CDCl₃)

δ (ppm): 3.25-3.54 (m, 2H) 5.14-5.38 (m, 3H) 5.72 (brs, 1H) 6.72 (t, J=9.4 Hz, 1H) 6.79 (d, J=7.8 Hz, 1H) 7.30-7.46 (m, 5H) 7.51 (brs, 1H).

(5) Synthesis of N-[(1S)-2,2,5,7-tetrafluoro-2,3-dihydro-1H-inden-1-yl]sulfamide

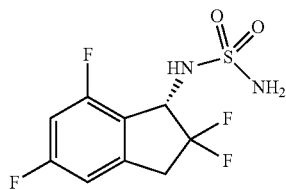

Palladium-carbon (10 w/w %, 30 mg, 0.028 mmol) was added to a solution of the product obtained in Production example 1-(4) (310 mg, 0.741 mmol) in MeOH (5 mL) and AcOEt (5 mL) at room temperature. The resulting solution was stirred for 30 reins at room temperature under H₂ atmosphere. AcOEt was added to the reaction mixture, and filtered through Celite® to remove palladium-carbon. The filtrate was concentrated in vacuo. The residue was purified by flash column chromatography (Yamazen HI-FLASH™ column Silicagel M size, 10 mL/min, gradient 30% to 70% AcOEt in n-heptane) to afford the title compound as a racemate (181 mg, 0.637 mmol). Optical resolution of the obtained racemate (180 mg, 0.633 mmol) was conducted by HPLC (CHIRALPAK™ IA, 20 mm I.D.×250 mm, 10 mL/min, 15% EtOH in hexane) to afford S-form of the title compound as white solids (76 mg, 0.267 mmol. 98% ee), that was eluted second with retention time of 44 min among the 2 isomers.

ESI-MS; m/z 307 [M+Na]⁺.

¹H-NMR (400 MHz, CDCl₃) δ (ppm): 3.32-3.60 (m, 2H), 4.70 (brs, 2H), 4.93 (d, J=9.3 Hz, 1H), 5.30 (q, J=9.3 Hz, 1H), 6.70-6.86 (m, 2H).

Production Example 2

Synthesis of (–)-N-(7-chloro-2,2,5-trifluoro-2,3-dihydro-1H-inden-1-yl)sulfamide

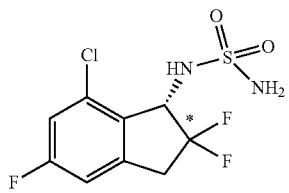 [SMILES: NS(=O)(=O)N[C@H]1c2c(Cl)cc(F)cc2CC1(F)F]

(1) Synthesis of 7-chloro-2,5-difluoro-2,3-dihydro-1H-inden-1-one

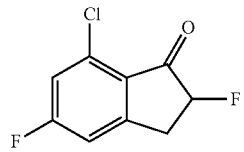

Selectfluor™ (2.49 g, 7.02 mmol) was added to a solution of 7-chloro-5-fluoro-1-indanone (CAS No. 1260008-48-7, 1.08 g, 5.85 mmol) in MeOH (30 mL) at room temperature. The mixture was refluxed for 2 hours. After cooling to room temperature, the solvent was evaporated under reduced pressure. To the residue was added DCM and the insoluble matter was filtered off. The filtrate was concentrated in vacuo. The residue was dissolved in MeCN (20 mL) and 5 N HCl (10 mL) and the solution was stirred at mom temperature for 1 hour. After concentration of the solution in vacuo, the residue was partitioned between AcOEt and H₂O. The organic layer was washed with brine, dried over MgSO₄, and filtrated. The filtrate was concentrated in vacuo to afford the title compound (1.13 g, 5.58 mmol).

¹H-NMR (400 MHz, CDCl₃) δ(ppm): 3.13-3.33 (m, 1H) 3.47-3.71 (m, 1H) 5.25 (ddd, J=51.0, 8.0, 4.5 Hz, 1H) 7.07 (dt, J=7.6, 2.0 Hz, 1H) 7.14 (dd, J=8.8, 2.0 Hz, 1H).

(2) Synthesis of 7-chloro-2,2,5-trifluoro-2,3-dihydro-1H-inden-1-one

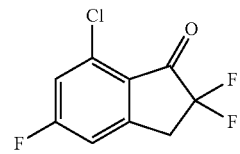

t-Butyldimethylsilyl trifluoromethanesulfonate (2.56 mL, 11.2 mmol) was added to a solution of the product obtained in Production example 2-(1) (1.13 g, 5.58 mmol) and TEA (3.11 mL 22.3 mmol) in DCM (30 mL) at 0° C. The mixture was stirred at room temperature for 2 hours. The reaction mixture was diluted with diethyl ether and saturated aqueous Na₂CO₃, and the layers were separated. The organic layer was successively washed with 1N HCl, saturated aqueous Na₂CO₃ and brine, and dried over Na₂SO₄. After filtration, the solvent was evaporated in vacuo. The residue was dissolved in MeCN (30 mL), and Selectfluor™ (2.17 g, 6.11 mmol) was added at room temperature. The mixture was stirred at room temperature for 3 hours, and then the resulting mixture was evaporated under reduced pressure. To the residue was added DCM and insoluble matter was filtered off. The solvent was evaporated in vacuo. The residue was purified by flash column chromatography (Yamazen HI-FLASH™ column Silicagel L size, 20 mL/min, gradient 0% to 30% AcOEt in n-heptane) to afford the title compound (2) (1.11 g, 5.03 mmol).

¹H-NMR (400 MHz, CDCl₃) δ (ppm): 3.47-3.63 (m, 2H) 7.06-7.13 (m, 1H) 7.17-7.23 (m, 1H).

(3) Synthesis of 7-chloro-2,2,5-trifluoro-2,3-dihydro-1H-inden-1-amine

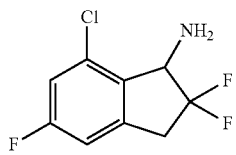

Ammonium acetate (11.5 g, 150 mmol) was added to a solution of the product obtained in Production example 2-(2) (1.10 g, 4.98 mmol) in isopropanol (40 mL) at room temperature. The mixture was refluxed for 30 mins. Sodium cyanoborohydride (940 mg, 15.0 mmol) was added to the reaction mixture and the mixture was heated under reflux for 12 hours. After cooling to room temperature, the reaction mixture was diluted with AcOEt, and 2N NaOH was added. The layers were separated and the organic layer was concentrated in vacuo. To the residue was added water, AcOEt and 1N HCl, and the layers were separated. The aqueous layer was basified with 2N NaOH and extracted with AcOEt. The organic layer was dried over Na₂SO₄. After filtration, the solvent was evaporated in vacuo. The residue was purified by flash column chromatography (Yamazen HI-FLASH™ column Silicagel L size, 20 mL/min, gradient 10% to 50% AcOEt in n-heptane) to afford the title compound (3) (699 mg, 3.15 mmol).

¹H-NMR (400 MHz, CDCl₃) δ (ppm): 3.24-3.41 (m, 1H) 3.47-3.65 (m, 1H) 4.50 (d, J=14.6 Hz, 1H) 6.85-6.93 (m, 1H) 7.02 (dd, J=9.0, 2.2 Hz, 1H).

(4) Synthesis of t-butyl N-(7-chloro-2,2,5-trifluoro-2,3-dihydro-1H-inden-1-yl)sulfamoylcarbamate

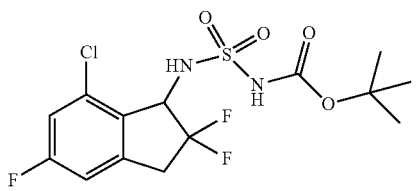 [SMILES: CC(C)(C)OC(=O)NS(=O)(=O)NC1c2c(Cl)cc(F)cc2CC1(F)F]

[(t-butoxy)carbonyl]{[4-(dimethyliminio)pyridin-1(4H)-yl]sulfonyl}amide (CAS No. 872496-91-8, 1.90 g, 6.31 mmol, prepared according to the method described in Organic Letters, 3, 2241 (2001)) and TEA (1.76 mL, 12.6 mmol) was added to a solution of the product obtained in Production example 2-(3) (699 mg, 3.15 mmol) in DCM (20 mL) at room temperature. The resulting mixture was heated for 12 hours under reflux. After cooling to room temperature, to the reaction mixture was added AcOEt and 1N HCl and the layers were separated. The organic layer was dried over MgSO₄. After filtration, the solvent was evaporated in vacuo. The residue was purified by silicagel column chromatography (Silicagel, 30% AcOEt in n-heptane) to afford the title compound (4) (1.08 g, 2.69 mmol).

¹H-NMR (400 MHz, CDCl₃)
δ (ppm): 1.49 (s, 9H) 3.28-3.55 (m, 2H) 5.07-5.36 (m, 1H) 5.51-5.70 (m, 1H) 6.89 (d, J=7.8 Hz, 1H) 7.07 (d, J=9.2 Hz, 1H) 7.29 (brs, 1H).

(5) Synthesis of (-)-N-(7-chloro-2,2,4-trifluoro-2,3-dihydro-1H-inden-1-yl)sulfamide

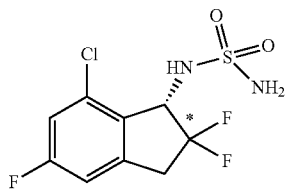 [SMILES: NS(=O)(=O)N[C@H]1c2c(Cl)cc(F)cc2CC1(F)F]

To a solution of the product obtained in Production example 2-(4) (1.08 g, 2.69 mmol) in AcOEt (25 mL) was added 4N HCl in AcOEt (26.9 ml, 108 mmol) and the mixture was stirred at room temperature for 5 hours. The solvent was evaporated in vacuo and the residue was purified by silicagel flash column chromatography (Yamazen HI-FLASH™ column L size, 20 mL/min, gradient 30% to 70% AcOEt in n-heptane) to afford the title compound as a racemate (627 mg, 2.09 mmol). Optical resolution of the obtained racemate (200 mg, 0.665 mmol) was conducted by HPLC (CHIRALPAK™ 113, 20 mm I.D.×250 mm, 10 ml/min, 10% EtOH in n-hexane) to afford the title (-)-form (83 mg, 0.276 mmol, 96% ee), which was eluted second with retention time of 49 min among the 2 optical isomers.

ESI-MS; m/z: 323[M+Na]⁺
¹H-NMR (400 MHz, CDCl₃) δ (ppm): 3.35-3.64 (m, 2H), 4.74 (brs, 2H), 4.86 (d, J=8.6 Hz, 1H), 5.07-5.28 (m, 1H), 6.83-6.95 (m, 1H), 7.09 (dd, J=8.7, 2.3 Hz, 1H).

Production Example 3

N-[(1S)-2,2-difluoro-7-methyl-2,3-dihydro-1H-inden-1-yl]sulfamide

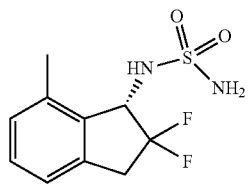 [SMILES: Cc1cccc2c1[C@H](NS(N)(=O)=O)C(F)(F)C2]

(1) Synthesis of 2-fluoro-7-methyl-2,3-dihydro-1H-inden-1-one

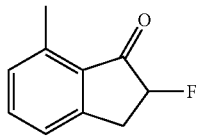

To a solution of 7-methyl-1-indanone (CAS No. 39627-61-7, 513 mg, 3.51 mmol) in MeOH (18 mL) was added Selectfluor™ (1.49 g, 4.21 mmol) at room temperature. The reaction mixture was heated for 2 hours under reflux. After cooling to room temperature, the solvent was evaporated under reduced pressure. The residue was treated with DCM and the insoluble matter was filtered off. The filtrate was concentrated in vacuo. The residue was dissolved in MeCN (10 mL) and 5 N HCl (5 mL). The solution was stirred at room temperature for 30 mins. After concentration of the solution in vacuo, the residue was partitioned between AcOEt and H$_2$O. The aqueous layer was extracted with AcOEt twice. The combined organic layers were washed with brine, dried over MgSO$_4$, filtered and concentrated in vacuo to afford the title compound (555 mg, 3.38 mmol).

$^1$H NMR (400 MHz, CDCl$_3$) δ ppm 2.64 (s, 3H), 3.18 (ddd, J=23.4, 16.8, 4.3 Hz, 1H), 3.57 (ddd, J=16.8, 7.8, 7.5 Hz, 1H), 5.21 (ddd, J=51.2, 7.8, 4.3 Hz, 1H), 7.17 (d, J=7.4 Hz, 1H), 7.26 (d, J=7.4 Hz, 1H), 7.51 (t, J=74 Hz, 1H).

(2) Synthesis of 2,2-difluoro-7-methyl-2,3-dihydro-1H-inden-1-one

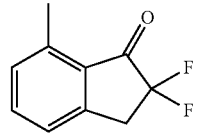

tert-Butyldimethylsilyl trifluoromethanesulfonate (1.55 mL 6.74 mmol) was added to a solution of the product obtained in Production example 3-(1) (555 mg, 3.38 mmol) and TEA (1.88 mL, 13.49 mmol) in DCM (30 mL) at 0° C. The mixture was stirred at room temperature for 1.5 hours. The reaction was quenched with sat. NaHCO$_3$, and the layers were separated. The aqueous layer was extracted with DCM. The combined organic layers were washed with brine and dried over MgSO$_4$. The insoluble matter was filtered off and the filtrate was concentrated in vacuo. The residue was dissolved in MeCN (20 mL), and Selectfluor™ (1.32 g, 3.73 mmol) was added at room temperature. After the reaction mixture was stirred for 1 h at room temperature, the solvent was evaporated under reduced pressure. The residue was dissolved in DCM and insoluble matter was filtered off. The filtrate was concentrated in vacuo. The residue was purified by silicagel flash column chromatography (Yamazen HI-FLASH™ column L size, 20 mL/min, gradient 15% to 20% AcOEt in n-heptane) to afford the title compound (563 mg, 3.09 mmol).

$^1$H-NMR (400 MHz, CDCl$_3$) δ ppm 2.66 (s, 3H), 3.51 (t, J=13.1 Hz, 1H), 7.23 (d, J=7.8 Hz, 1H), 7.28 (d, J=7.8 Hz, 1H), 7.57 (t, J=7.8 Hz, 1H).

(3) Synthesis of 2,2-difluoro-7-methyl-2,3-dihydro-1H-inden-1-ol

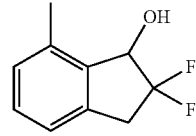

To a solution of the product prepared by the method described in Production example 3-(2) (1.09 g, 5.99 mmol) in MeOH (20 mL) was added sodium borohydride (453 mg, 12.0 mmol) at 0° C. After stirring for 45 minutes at the same temperature, water and AcOEt was added to the reaction mixture, and the layers were separated. The separated aqueous layer was extracted with AcOEt twice. The combined organic layer was washed with brine, and dried over MgSO$_4$. After filtration, the filtrate was concentrated and dried in vacuo to afford the title compound (1.05 g, 5.72 mmol).

$^1$H-NMR (400 MHz, CDCl$_3$) δ (ppm): 2.23 (br. s, 1H), 2.43 (s, 3H), 3.26-3.39 (m, 1H), 3.44-3.58 (m, 1H), 5.08-5.15 (m, 1H), 7.07 (d, J=7.8 Hz, 1H), 7.10 (d, J=7.8 Hz, 1H), 7.23-7.26 (m, 1H).

(4) Synthesis of 1-azido-2,2-difluoro-7-methyl-2,3-dihydro-1H-inden

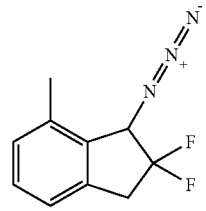

TEA (3.59 ml, 25.8 mmol) and chloromethanesulfonyl chloride (1.02 ml, 11.4 mmol) were added to a solution of the product obtained in Production example 3-(3) (1.05 g, 5.72 mmol) in DCM (25 mL) at 0° C. After stirring for 2 hours at room temperature, the reaction mixture was diluted with diethyl ether and quenched with sat. NaHCO$_3$. The aqueous layer was extracted with diethyl ether for 3 times. The combined organic layer was washed with brine and dried over MgSO$_4$. The extract was filtered and concentrated in vacuo. The residue was dissolved in DMF (50 mL), and sodium azide (753 mg, 11.6 mmol) was added to the solution at room temperature. The reaction mixture was stirred for 2 hours at 70° C. After cooling the mixture to room temperature, water and diethyl ether were added. The layers were separated, and the aqueous layer was extracted with diethyl ether for 3 times. The combined organic layer was washed with water and brine, and dried over MgSO$_4$. The extract was filtered and concentrated in vacuo. The residue was purified by silicagel flash column chromatography (Yamazen HI-FLASH™ column L size, 20 mL/min, 20% AcOEt in n-heptane) to afford the title compound (641 mg, 3.06 mmol).

$^1$H-NMR (400 MHz, CDCl$_3$) δ ppm: 2.41 (s, 3H), 3.30-3.43 (m, 1H), 3.51 (ddd, J=20.3, 16.8, 10.9 Hz, 1H), 4.77 (d, J=13.3 Hz, 1H), 7.09 (d, J=7.8 Hz, 1H), 7.14 (d, J=7.8 Hz, 1H), 7.26-7.31 (m, 1H).

(5) Synthesis of N-(2,2-difluoro-7-methyl-2,3-dihydro-1H-inden-1-yl)sulfamide

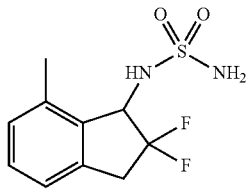 [SMILES: Cc1cccc2c1C(NS(N)(=O)=O)C(F)(F)C2]

To a solution of the product obtained in Production example 3-(4) (641 mg, 3.06 mmol) in water (4 ml) and tetrahydrofuran (16 ml) was added triphenyl phosphine (1.21 g, 4.61 mmol) at room temperature. The reaction mixture was stirred for 1 hour at 80° C. After cooling to room temperature, AcOEt (20 mL) and 1N HCl (20 mL) were added. The separated organic layer was extracted with 10 mL of 1N HCl twice. The aqueous layer was combined and basified with 20 mL of 2N NaOH. The layer was extracted with AcOEt for 3 times and the combined organic layer was washed with brine and dried over MgSO$_4$. The extract was filtered and concentrated in vacuo. To a solution of the residue and TEA (1.1 mL, 7.89 mmol) in DCM (26 mL), sulfamoyl chloride (CAS No. 7778-42-9, 915 mg, 7.92 mmol, prepared according to the method described in US2008/96903) was added in small portions at room temperature. The reaction mixture was subsequently stirred for 1 hour at room temperature. To the mixture was added 20 mL of 1N HCl, and the aqueous layer was extracted with DCM twice. The combined organic layer was dried over MgSO$_4$, filtered and concentrated in vacuo. The residue was purified by silicagel flash column chromatography (Yamazen HI-FLASH™ column L size, 20 mL/min, gradient 50% to 65% AcOEt in n-heptane) to afford the title compound (348 mg, 1.33 mmol).

$^1$H-NMR (400 MHz, CDCl$_3$) δ ppm: 2.45 (s, 3H), 3.32-3.56 (m, 2H), 4.70-4.80 (m, 3H), 5.17-5.26 (m, 1H), 7.06 (d, J=7.4 Hz, 1H), 7.12 (d, J=7.4 Hz, 1H), 7.23-7.29 (m, 1H).

(6) Synthesis of N-[(1S)-2,2-difluoro-7-methyl-2,3-dihydro-1H-inden-1-yl]sulfamide

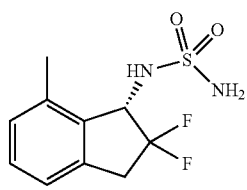 [SMILES: Cc1cccc2c1[C@H](NS(N)(=O)=O)C(F)(F)C2]

Optical resolution of the racemate obtained in Production example 3-(5) (348 mg, 1.33 mmol) was conducted by HPLC (CHIRALPAK™ IA, 20 mm I.D.×250 mm, 10 ml/min, 15% EtOH in n-hexane) to afford the title compound (1S)-form (107 mg, 0.409 mmol; >99% ee) as white solids, that was eluted second with retention time of 25 min among the 2 optical isomers.

ESI-MS m/z: 285[M+Na]$^+$ $^1$H-NMR (400 MHz, CDCl$_3$) δ ppm: 2.45 (s, 3H), 3.32-3.56 (m, 2H), 4.70-4.80 (m, 3H), 5.17-5.26 (m, 1H), 7.06 (d, J=7.4 Hz, 1H), 7.12 (d, J=7.4 Hz, 1H), 7.23-7.29 (m, 1H).

Production Example 4

Synthesis of N-[(1S)-2,2,5-Trifluoro-7-methyl-2,3-dihydro-1H-inden-1-yl]sulfamide

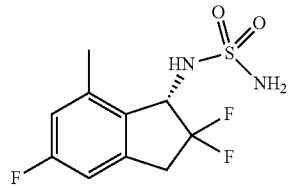 [SMILES: Cc1cc(F)cc2c1[C@H](NS(N)(=O)=O)C(F)(F)C2]

(1) Synthesis of 7-bromo-2,2,5-trifluoro-2,3-dihydro-1H-inden-1-one

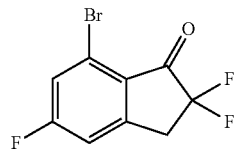

The title compound (5.10 g, 19.2 mmol) was obtained from 7-bromo-5-fluoro-1-indanone (CAS No. 1260016-95-2, 4.55 g, 19.9 mmol) by a similar method as described in Production example 1-(1) and 1-(2).

$^1$H NMR (400 MHz, CDCl$_3$) δ (ppm): 3.53 (t, J=12.5 Hz, 2H), 7.14 (d, J=7.6 Hz, 1H), 7.41 (d, J=8.4 Hz, 1H).

(2) Synthesis of 7-bromo-2,2,5-trifluoro-2,3-dihydro-1H-inden-1-ol

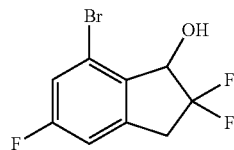 [SMILES: OC1c2c(Br)cc(F)cc2CC1(F)F]

The title compound (4.78 g, 17.9 mmol) was obtained from the product obtained in Production example 4-(1) (5.10 g, 19.2 mmol) by a similar method as described in Production example 3-(3).

$^1$H-NMR (400 MHz, CDCl$_3$) δ (ppm): 2.50 (s, 1H), 3.38 (td, J=17.0, 2.7 Hz, 1H), 3.50-3.69 (m, 1H), 5.06 (dd, J=12.5, 4.3 Hz, 1H), 6.95 (dd, J=8.0, 1.0 Hz, 1H), 7.22 (dd, J=8.6, 2.3 Hz, 1H).

(3) Synthesis of 2-[(7-bromo-2,2,5-trifluoro-2,3-dihydro-1H-inden-1-yl)oxy]tetrahydro-2H-pyran

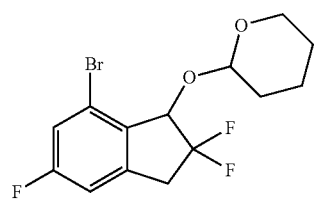 [SMILES: Fc1cc(Br)c2c(c1)CC(F)(F)C2OC1CCCCO1]

To a solution of the product obtained in Production example 4-(2) (2.78 g, 10.4 mmol) and 3,4-dihydro-2H-pyran (2.18 mL, 23.9 mmol) in DCM (40 ml) was added PPTS (52 mg, 0.208 mmol) at room temperature. And the reaction mixture was stirred for 86 hours at room temperature. The solvent was evaporated in vacuo and the residue was purified by silicagel flash column chromatography (Yamazen HI-FLASH™ column M size, 10 mL/min, gradient 10% to 25% AcOEt in n-heptane) to afford the title compound (3.42 g, 9.74 mmol) as about a 1:1 mixture of racemic diastereomers.

$^1$H-NMR (400 MHz, CDCl$_3$) δ (ppm): 1.51-1.84 (m, 6H), 3.26-3.52 (m, 1H), 3.52-3.68 (m, 2H), 4.05-4.19 (m, 1H), 5.00-5.21 (m, 2H), 6.92 (d, J=8.2 Hz, 1H), 7.21 (dt, J=8.2, 2.6 Hz, 1H).

(4) Synthesis of 2-[(2,2,5-trifluoro-7-methyl-2,3-dihydro-1H-inden-1-yl)oxy]tetrahydro-2H-pyran

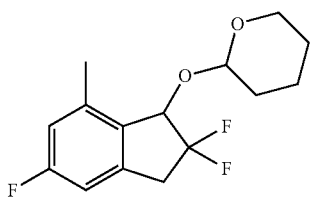 [SMILES: Cc1cc(F)cc2c1C(OC1CCCCO1)C(F)(F)C2]

To a solution of the product obtained in Production example 4-(3) (1.70 g, 4.84 mmol) in 1,4-dioxane (10 ml) was added dropwise a 2M n-hexane solution of dimethyl zinc (4.84 ml, 9.68 mmol). Then, after addition of [1,1'-bis(diphenylphosphino)ferrocene]dichloro palladium(II) (177 mg, 0.242 mmol), the reaction mixture was stirred for 3 hours at 100° C. under nitrogen atmosphere. After cooling to room temperature, water was added and the mixture was extracted with AcOEt. The organic layer was washed with brine and dried over anhydrous Na$_2$SO$_4$. The insoluble matter was filtered off and the filtrate was evaporated in vacuo. The residue was purified by silicagel flash column chromatography (Yamazen HI-FLASH™ column Silicagel M size, 10 ml/min, gradient 0% to 25% AcOEt in n-heptane) to afford the title compound as about a 1:1 mixture of racemic diastereomers (1.06 g, 3.70 mmol).

ESI-MS; m/z: 309[M+Na]$^+$
$^1$H-NMR (400 MHz, CDCl$_3$) δ (ppm): 1.51-1.90 (m, 6H), 2.35 (s, 1.5H), 2.43 (s, 1.5H), 3.19-3.29 (m, 1H), 3.45-3.64 (m, 2H), 3.98-4.11 (m, 1H), 4.88 (t, J=3.4 Hz, 0.5H), 4.95 (d, J=5.1 Hz, 0.5H), 5.01 (dd, J=11.6, 2.8 Hz, 0.5H), 5.16 (d, J=11.7 Hz, 0.5H), 6.74-6.81 (m, 2H)

(5) Synthesis of 2,2,5-trifluoro-7-methyl-2,3-dihydro-1H-inden-1-ol

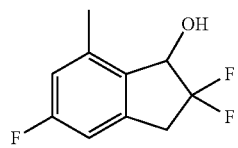

To a solution of the product obtained in Production example 4-(4) (1.06 g, 3.70 mmol) in MeOH (10 ml) was added PPTS (46 mg, 0.185 mmol). And the reaction mixture was stirred for 1 hour at 60° C. After cooling to room temperature, saturated NaHCO$_3$ was added to the reaction mixture and the mixture was extracted with AcOEt. The organic layer was washed with brine and dried over anhydrous Na$_2$SO$_4$. The insoluble matter was filtered off and the filtrate was evaporated in vacuo. The residue was purified by silicagel flash column chromatography (Yamazen HI-FLASH™ column M size, 10 mL/min, gradient 5% to 25% AcOEt in n-heptane) to afford the title compound (692 mg, 3.42 mmol).

$^1$H-NMR (400 MHz, CDCl$_3$) δ (ppm): 2.23 (dd, J=5.7, 2.5 Hz, 1H), 2.42 (s, 3H), 3.30 (td, J=16.8, 5.2 Hz, 1H), 3.50 (td, J=16.8, 11.6 Hz, 1H), 5.05 (dd, J=12.1, 5.1 Hz, 1H), 6.77 (d, J=8.2 Hz, 1H), 6.82 (d, J=10.2 Hz, 1H).

(6) Synthesis of 1-Azido-2,2,5-trifluoro-7-methyl-2,3-dihydro-1H-inden

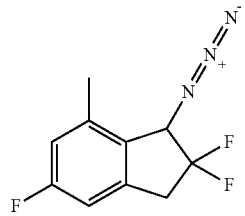

To a solution of the product obtained in Production example 4-(5) (692 mg, 3.42 mmol) and TEA (1.43 ml, 10.3 mmol) in DCM (10 ml) was added chloromethanesulfonyl chloride (765 mg, 5.13 mmol) at 0° C. And the reaction mixture was stirred for 2 hours at room temperature. To the reaction mixture was added saturated NaHCO$_3$ and the mixture was extracted with diethyl ether. The organic layer was successively washed with 1N HCl and brine then dried over anhydrous Na$_2$SO$_4$. After filtration, the filtrate was evaporated in vacuo. To a solution of the residue in DMF (10 ml) was added sodium azide (442 mg, 6.80 mmol) at room temperature, and the mixture was stirred for 2 hours at 70° C. After cooling to room temperature, the mixture was partitioned between diethyl ether and H$_2$O. The aqueous layer was extracted with diethyl ether. The combined organic layer was washed with brine and dried over anhydrous Na$_2$SO$_4$. After filtration, the filtrate was evaporated in vacuo. The residue was purified by silicagel flash column chromatography (Yamazen HI-FLASH™ column M size, 10 mL/min, gradient 10% to 30% AcOEt in n-heptane) to afford the title compound (320 mg, 1.41 mmol).

$^1$H-NMR (400 MHz, CDCl$_3$)
δ (ppm): 2.41 (s, 3H), 3.30-3.56 (m, 2H), 4.74 (d, J=13.3 Hz, 1H), 6.81 (d, J=7.8 Hz, 1H), 6.86 (d, J=9.4 Hz, 1H).

(7) Synthesis of 2,2,5-trifluoro-7-methyl-2,3-dihydro-1H-inden-1-amine

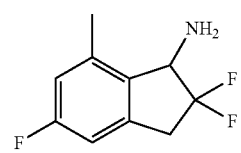

To a solution of the product obtained in Production example 4-(6) (320 mg, 1.41 mmol) in water (1 ml) and THF (5 nil) was added triphenylphosphine (554 mg, 2.11 mmol) at room temperature, and the mixture was stirred for 2 hours at 80° C. After cooling to room temperature, the mixture was partitioned between AcOEt and 1N HCl. The obtained aqueous layer was basified with 5N NaOH. The aqueous layer was extracted with AcOEt for 3 times and the combined extract was dried over anhydrous $Na_2SO_4$. After filtration, the filtrate was concentrated in vacuo to afford the title compound (180 mg, 0.895 mmol).

ESI-MS; m/z: 202 [M+H]$^+$ (8) Synthesis of tert-butyl N-(2,2,5-trifluoro-7-methyl-2,3-dihydro-1H-inden-1-yl)sulfamoylcarbamate

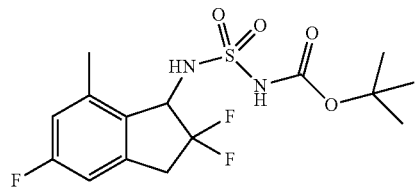 [SMILES: Cc1cc(F)cc2c1C(NS(=O)(=O)NC(=O)OC(C)(C)C)C(F)(F)C2]

To a solution of the product in Production example 4-(7) (180 mg, 0.895 mmol) in DCM (10 mL) were added [(tert-butoxy)carbonyl]{[4-(dimethyliminio)pyridin-1 (4H)-yl]sulfonyl}amide (297 mg, 0.984 mmol) and TEA (0.374 mL, 2.68 mmol) at room temperature. The resulting mixture was heated under reflux for 65.5 hours. After cooling to room temperature, the mixture was partitioned between AcOEt and 1N HCl. The organic layer was dried over anhydrous $Na_2SO_4$, filtrated and evaporated in vacuo to afford the title compound (257 mg, 0.676 mmol).

ESI-MS; m/z: 403 [M+Na]$^+$ (9) Synthesis of N-[(1S)-2,2,5-trifluoro-7-methyl-2,3-dihydro-1H-inden-1-yl]sulfamide

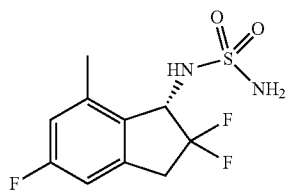 [SMILES: Cc1cc(F)cc2c1[C@H](NS(N)(=O)=O)C(F)(F)C2]

To a solution of the product in Production example 4-(8) (257 mg, 0.676 mmol) in MeOH (4 mL) was added 4N HCl in AcOEt (3.38 ml, 13.5 mmol) at room temperature and stirred for 14 hours. The solvent was evaporated in vacuo and the residue was purified by silicagel column chromatography (AcOEt) to afford the title compound (162 mg, 0.578 mmol) as a racemate. Optical resolution of the obtained racemate (162 mg, 0.578 mmol) was conducted by HPLC (CHIRALPAK™ IF, 20 mm I.D.×250 mm, 10 mL/min, 10% EtOH in n-hexane) to afford the title (S)-isomer (71 mg, 0.253 mmol; 98% ee) as white solids, which was eluted second with retention time of 30 min among the 2 optical isomers.

ESI-MS; m/z: 303[M+Na]$^+$ $^1$H-NMR (400 MHz, DMSO-d$_6$) δ (ppm): 2.37 (s, 3H), 3.20-3.31 (m, 1H), 3.38-3.64 (m, 1H), 4.79 (dd, J=14.3, 8.8 Hz, 1H), 6.77 (s, 2H), 6.90-7.03 (m, 2H), 7.51 (d, J=9.0 Hz, 1H).

Reference Example 1

X-ray Crystallographic Analysis of N-[(1S)-2,2,5,7-tetrafluoro-2,3-dihydro-1H-inden-1-yl]sulfamide The white solids obtained in Production example 1-(5) were dissolved in MeOH and toluene, and recrystallized by solvent evaporation method. X-ray diffraction analysis was conducted using the obtained single crystal. The results of data collection and crystallographic analysis are summarized in Table 1, and the atomic coordinates are shown in Tables 2. The absolute configuration of the title compound was specified from such results.

TABLE 1

| | |
|---|---|
| Temperature | 100 K |
| Wavelength | 0.7107 Å |
| Crystal system, space group | Monoclinic, I2 |
| Lattice parameters | a = 12.975 (7) Å |
| | b = 4.963 (3) Å |
| | c = 33.74 (2) Å |
| | β = 98.15 (2)° |
| Volume | 2151 (2) Å$^3$ |
| Z value, calculated density | 8, 1,755 g/cm$^3$ |
| Crystal dimensions | 0.20 × 0.10 × 0.10 mm |
| Total number of reflections/number of unique reflections | 7908/4056 [R$_{int}$ = 0.0412] |
| Completeness | 70.1% |
| Structure solution | Direct methods (SHELX97) |
| Refinement | Full-matrix least-squares on F$^2$ |
| Reflection/parameter | 4056/341 |
| Goodness of fit indicator | 1.066 |
| R factor (all data) | 0.0398 |
| R factor (I > 2σ (I)) | 0.0389 |
| Flack parameter | −0.12(8) |
| The maximum and minimum peaks on the final difference Fourier map | 0.52 and −0.47 e/Å$^3$ |

TABLE 2

| Atom | x | y | z | B (eq) |
|---|---|---|---|---|
| S1 | 0.66860(5) | 1.1453(2) | 0.04848(2) | 0.523(13) |
| S2 | 0.33982(5) | −0.3815(2) | 0.08182(2) | 0.534(13) |
| F1 | 0.9462(2) | 1.1782(6) | 0.03401(6) | 2.55(5) |
| F2 | 0.8837(2) | 0.7746(5) | 0.02197(5) | 1.94(4) |
| F3 | 1.0477(2) | 0.1913(5) | 0.18786(5) | 1.72(4) |
| F4 | 0.76903(13) | 0.7856(5) | 0.15680(5) | 1.45(4) |
| F5 | 0.2629(2) | −0.4533(5) | 0.18975(6) | 1.63(4) |
| F6 | 0.22095(13) | −0.0561(5) | 0.16562(6) | 1.79(4) |
| F7 | 0.6409(2) | 0.5667(5) | 0.24296(7) | 3.28(6) |
| F8 | 0.5767(2) | 0.0236(5) | 0.12874(6) | 1.73(4) |
| O1 | 0.6856(2) | 1.3908(5) | 0.07134(6) | 0.87(4) |
| O2 | 0.5685(2) | 1.0201(5) | 0.04407(6) | 0.83(4) |
| O3 | 0.2877(2) | −0.6171(5) | 0.09423(6) | 1.04(4) |
| O4 | 0.2906(2) | −0.2444(5) | 0.04672(6) | 1.01(4) |
| N1 | 0.7474(2) | 0.9234(6) | 0.06963(7) | 0.63(4) |
| N2 | 0.6931(3) | 1.2225(7) | 0.00419(8) | 1.42(6) |
| N3 | 0.3529(2) | −0.1541(6) | 0.11579(7) | 0.89(5) |
| N4 | 0.4581(2) | −0.4747(7) | 0.08027(8) | 1.04(5) |
| C1 | 0.8556(2) | 0.9751(7) | 0.08358(8) | 0.71(5) |
| C2 | 0.9295(3) | 0.9382(8) | 0.05181(9) | 1.30(6) |
| C3 | 1.0297(3) | 0.8054(8) | 0.07165(9) | 1.22(6) |
| C4 | 0.9960(2) | 0.6698(7) | 0.10748(8) | 0.79(5) |
| C5 | 1.0477(2) | 0.4717(7) | 0.13193(9) | 0.93(6) |
| C6 | 1.0004(3) | 0.3878(7) | 0.16354(9) | 1.02(6) |
| C7 | 0.9074(3) | 0.4818(8) | 0.17276(9) | 1.16(6) |
| C8 | 0.8589(2) | 0.6795(8) | 0.14792(9) | 1.09(6) |
| C9 | 0.9001(2) | 0.7762(7) | 0.11510(9) | 0.71(5) |

TABLE 2-continued

| Atom | x | y | z | B (eq) |
|---|---|---|---|---|
| C10 | 0.3896(2) | −0.2109(7) | 0.15757(8) | 0.59(5) |
| C11 | 0.3017(3) | −0.2051(7) | 0.18443(9) | 0.95(5) |
| C12 | 0.3446(3) | −0.0697(8) | 0.22358(10) | 1.41(6) |
| C13 | 0.4388(3) | 0.0810(6) | 0.21379(9) | 0.82(5) |
| C14 | 0.4979(3) | 0.2722(8) | 0.23671(9) | 1.49(6) |
| C15 | 0.5824(3) | 0.3787(8) | 0.22139(11) | 1.97(7) |
| C16 | 0.6111(3) | 0.3013(8) | 0.18533(11) | 1.76(7) |
| C17 | 0.5503(3) | 0.1041(7) | 0.16364(9) | 1.03(6) |
| C18 | 0.4642(2) | −0.0010(7) | 0.17711(8) | 0.82(5) |
| H1 | 0.8635 | 1.1616 | 0.0948 | 0.85 |
| H2A | 1.0846 | 0.9410 | 0.0798 | 1.47 |
| H3B | 1.0558 | 0.6726 | 0.0536 | 1.47 |
| H4 | 1.1123 | 0.3988 | 0.1269 | 1.11 |
| H5 | 0.8778 | 0.4147 | 0.1950 | 1.39 |
| H6 | 0.7232 | 0.7605 | 0.0729 | 0.75 |
| H7 | 0.7480 | 1.3235 | 0.0061 | 1.17 |
| H8 | 0.6988 | 1.0969 | −0.0114 | 1.91 |
| H9 | 0.4243 | −0.3912 | 0.1598 | 0.71 |
| H10A | 0.3645 | −0.2047 | 0.2449 | 1.69 |
| H11B | 0.2929 | 0.0555 | 0.2324 | 1.69 |
| H12 | 0.4811 | 0.3279 | 0.2620 | 1.78 |
| H13 | 0.6696 | 0.3786 | 0.1756 | 2.11 |
| H14 | 0.3371 | 0.0132 | 0.1088 | 1.07 |
| H15 | 0.4673 | −0.6088 | 0.0648 | 2.80 |
| H16 | 0.4954 | −0.3328 | 0.0723 | 2.37 |

Reference Example 2

X-ray Crystallographic Analysis of N-[(1S)-2,2-difluoro-7-methyl-2,3-dihydro-1H-inden-1-yl]sulfamide The white solids obtained in Production example 3-(6) were dissolved in EtOH and n-hexane and recrystallized by temperature gradient to afford microcrystals. The microcrystals were dissolved in $Et_2O$ and further recrystallized by solvent evaporation method. X-ray diffraction analysis was conducted using the obtained single crystal. The results of data collection and crystallographic analysis are summarized in Table 3, and the atomic coordinates are shown in Tables 4. The absolute configuration of the title compound was specified from such results.

TABLE 3

| | |
|---|---|
| Temperature | 100 K |
| Wavelength | 1.5418 Å |
| Crystal system, space group | Monoclinic, $P2_1$ |
| Lattice parameters | a = 8.6474 (3) Å |
| | b = 7.6050 (2) Å |
| | c = 8.7054 (3) Å |
| | β = 100.345 (3)° |
| Volume | 563.19 (4) Å$^3$ |
| Z value, calculated density | 2, 1.546 g/cm$^3$ |
| Crystal dimensions | 0.20 × 0.10 × 0.10 mm |
| Total number of reflections/number of unique reflections | 5898/1998 [$R_{int}$ = 0.0479] |
| Completeness | 98.7% |
| Structure solution | Direct methods (SHELX97) |
| Refinement | Full-matrix least-squares on F$^2$ |
| Reflection/parameter | 1998/163 |
| Goodness of fit indicator | 1.128 |
| R factor (all data) | 0.0530 |
| R factor (I > 2σ (I)) | 0.0481 |
| Flack parameter | 0.02 (4) |
| The maximum and minimum peaks on the final difference Fourier map | 0.34 and −1.02 e/Å$^3$ |

TABLE 4

| Atom | x | y | z | B (eq) |
|---|---|---|---|---|
| S1 | 0.1572(1) | 0.4621(1) | 0.5199(1) | 1.79(3) |
| F2 | 0.0744(3) | 0.5656(4) | 0.8851(3) | 2.63(6) |
| F3 | 0.0241(3) | 0.2859(4) | 0.8642(3) | 2.62(6) |
| O5 | 0.1999(4) | 0.2897(4) | 0.4775(4) | 2.20(6) |
| O18 | 0.1789(4) | 0.6092(4) | 0.4240(4) | 2.46(6) |
| N6 | 0.2664(4) | 0.5054(4) | 0.6876(4) | 1.61(6) |
| N7 | −0.0242(5) | 0.4536(7) | 0.5286(4) | 2.14(7) |
| C8 | 0.1416(6) | 0.4043(6) | 0.9110(5) | 1.97(8) |
| C9 | 0.2761(5) | 0.3829(5) | 0.8175(5) | 1.47(7) |
| C10 | 0.4217(5) | 0.4048(6) | 0.9402(5) | 1.66(7) |
| C11 | 0.5787(5) | 0.4130(6) | 0.9159(5) | 2.10(8) |
| C12 | 0.6927(6) | 0.4239(6) | 1.0487(6) | 2.58(9) |
| C13 | 0.6581(6) | 0.4274(6) | 1.1999(6) | 2.64(9) |
| C14 | 0.5028(6) | 0.4174(6) | 1.2212(5) | 2.44(9) |
| C15 | 0.3858(6) | 0.4041(6) | 1.0885(5) | 1.98(8) |
| C16 | 0.2115(5) | 0.3830(7) | 1.0839(5) | 2.29(9) |
| C17 | 0.6204(6) | 0.4078(8) | 0.7548(6) | 3.0(1) |
| H4 | −0.067(5) | 0.377(7) | 0.559(5) | 0.0(8) |
| H6 | 0.3203 | 0.6041 | 0.7001 | 1.93 |
| H9 | 0.2736 | 0.2601 | 0.7759 | 1.76 |
| H12 | 0.7997 | 0.4293 | 1.0370 | 3.10 |
| H13 | 0.7406 | 0.4365 | 1.2877 | 3.16 |
| H14 | 0.4771 | 0.4196 | 1.3228 | 2.93 |
| H16A | 0.1713 | 0.4745 | 1.1475 | 2.75 |
| H16B | 0.1871 | 0.2656 | 1.1225 | 2.75 |
| H17A | 0.7336 | 0.3880 | 0.7636 | 3.64 |
| H17B | 0.5920 | 0.5200 | 0.7018 | 3.64 |
| H17C | 0.5626 | 0.3122 | 0.6945 | 3.64 |
| H19 | −0.070(8) | 0.55(1) | 0.551(9) | 4(2) |

Reference Example 3

X-ray Crystallographic Analysis of N-[(1S)-2,2,5-trifluoro-7-methyl-2,3-dihydro-1H-inden-1-yl]sulfamide The white solids obtained in Production example 4-(9) were dissolved in EtOH and recrystallized by vapor diffusion method using toluene as reservoir solution. X-ray diffraction analysis was conducted using the single crystal obtained as above.

The results of data collection and crystallographic analysis are summarized in Table 5, and the atomic coordinates are shown in Tables 6. The absolute configuration of the title compound was specified from such results.

TABLE 5

| | |
|---|---|
| Temperature | 100 K |
| Wavelength | 0.7107 Å |
| Crystal system, space group | Monoclinic, $P2_1$ |
| Lattice parameters | a = 4.708 (7) Å |
| | b = 7.495 (11) Å |
| | c = 15.66 (3) Å |
| | β = 90.926 (3)° |
| Volume | 553 (2) Å$^3$ |
| Z value, calculated density | 2, 1.684 g/cm$^3$ |
| Crystal dimensions | 0.20 × 0.20 × 0.02 mm |
| Total number of reflections/number of unique reflections | 6974/2195 [$R_{int}$ = 0.1065] |
| Completeness | 77.4% |
| Structure solution | Direct methods (SHELX97) |
| Refinement | Full-matrix least-squares on F$^2$ |
| Reflection/parameter | 2195/172 |
| Goodness of fit indicator | 1.132 |
| R factor (all data) | 0.0914 |
| R factor (I > 2σ (I)) | 0.0692 |
| Flack parameter | 0.0 (3) |
| The maximum and minimum peaks on the final difference Fourier map | 0.71 and −0.71 e/Å$^3$ |

TABLE 6

| Atom | x | y | z | B (eq) |
|------|---|---|---|--------|
| S1   | 1.2336(3)  | 0.2417(3)  | 0.09702(9) | 1.89(3)  |
| F1   | 1.0091(8)  | 0.0964(5)  | 0.2896(3)  | 2.14(7)  |
| F2   | 1.4190(8)  | 0.1968(6)  | 0.3304(3)  | 2.33(8)  |
| F3   | 0.3417(8)  | 0.8204(6)  | 0.4194(3)  | 2.60(8)  |
| O1   | 1.0577(10) | 0.1451(7)  | 0.0386(3)  | 2.31(9)  |
| O2   | 1.4639(10) | 0.1479(7)  | 0.1365(3)  | 2.21(9)  |
| N1   | 1.0183(11) | 0.3243(8)  | 0.1649(3)  | 1.79(10) |
| N2   | 1.3717(12) | 0.4204(9)  | 0.0564(4)  | 2.24(11) |
| C1   | 1.1199(13) | 0.3943(9)  | 0.2475(4)  | 1.75(11) |
| C2   | 1.1449(12) | 0.2475(10) | 0.3169(4)  | 1.80(10) |
| C3   | 1.012(2)   | 0.3159(10) | 0.3983(4)  | 1.94(11) |
| C4   | 0.8503(12) | 0.4786(9)  | 0.3690(4)  | 1.52(11) |
| C5   | 0.659(2)   | 0.5802(9)  | 0.4157(4)  | 1.80(11) |
| C6   | 0.5365(12) | 0.7227(10) | 0.3758(4)  | 1.63(11) |
| C7   | 0.6039(13) | 0.7793(9)  | 0.2942(4)  | 1.97(12) |
| C8   | 0.7994(12) | 0.6798(9)  | 0.2484(4)  | 1.65(11) |
| C9   | 0.916(2)   | 0.5260(9)  | 0.2861(4)  | 1.73(11) |
| C10  | 0.8837(13) | 0.7403(11) | 0.1616(4)  | 2.09(11) |
| H1   | 1.3090     | 0.4527     | 0.2402     | 2.10     |
| H2A  | 0.8836     | 0.2258     | 0.4229     | 2.32     |
| H3B  | 1.1601     | 0.3476     | 0.4414     | 2.32     |
| H4   | 0.6160     | 0.5510     | 0.4731     | 2.16     |
| H5   | 0.5189     | 0.8832     | 0.2702     | 2.36     |
| H6B  | 1.0913     | 0.7399     | 0.1579     | 2.51     |
| H7C  | 0.8122     | 0.8614     | 0.1515     | 2.51     |
| H8A  | 0.8030     | 0.6593     | 0.1185     | 2.51     |
| H9   | 0.8355     | 0.3277     | 0.1523     | 2.15     |
| H10  | 1.53(2)    | 0.404(12)  | 0.022(6)   | 4(2)     |
| H11  | 1.23(3)    | 0.49(2)    | 0.008(8)   | 7(3)     |

Pharmacological Test Examples

The present inventors conducted studies using the mice hot plate test to confirm an analgesic effect on acute pain and using the rat chronic constriction injury (CCI) model to confirm analgesic effect on chronic pain, respectively. In addition, the present inventors conducted a study using the mice formalin test to confirm an analgesic effect on acute persistent pain.

The compound disclosed in Example 1 of Patent Literature 1, (N-(benzo[b]thiophen-3-ylmethyl)sulfamide), and the compound disclosed in Example 7 of Patent Literature 2, ((2S)-(−)-N-(6-chloro-2,3-dihydro-benzo[1,4]dioxin-2-ylmethyl)-sulfamide), were prepared according to Patent Literatures 1 and 2 and used as reference compounds (1 and 2), respectively.

Test Example 1

Mice Hot-plate Test

The mice hot-plate test was performed to determine the efficacy on acute pain. In this model, latency to the first pain response is recorded as a measure of pain sensitivity (Malmberg, A. and Yaksh, T., Pain. 1995, 60: 83-90).

<Methods>

Male C57BL/6NCrlCrlj mice (Charles River Japan) aged 6 weeks (n=4 to 10, for each treatment) were used for this experiment. The hot plate (model MK 350, Muromachi Kikai Co. Ltd) was set to 53° C. For oral administration, the test compound was suspended in an aqueous solution containing 0.45% methyl cellulose/4.5% Cremophor/10% dimethyl sulfoxide to prepare a suspension having a dosing volume of 10 ml/kg and the suspension was administered orally 60 minutes before the hot-plate test Morphine was used as a positive control and the mixed solvent (vehicle) alone not containing the test compound was used as a negative control.

Each mouse was placed on the hot plate and a stopwatch was immediately started for measurement. The latency time to the first pain response (paw lick or escape jump) was measured. The cut-off time was set to 30 seconds in order to avoid overdamage of the tissues, and the mouse was immediately removed from the hot-plate after measurement. All data are expressed as the mean±SEM. All statistical analyses were performed using Holm-Sidak's multiple comparisons test. The p-values less than 0.05 were judged as statistically significant in this experiment.

<Results>

The results of the mice hot plate test are shown in FIG. 1. The latency times to the first pain response were significantly increased by pre-administration of Test Compounds 1, 2, 3 and 4. These results show an analgesic effect of the test compounds on acute pain.

Test Example 2

Rat Chronic Constriction Injury (CCI) Model

The rat chronic constriction injury (CCI) model was used to determine the efficacy on the chronic pain. In this model, tactile allodynia, a typical symptom in chronic pain patients, can be evaluated by using a response threshold against mechanical stimulation by von Frey filaments as an index (Bennett G. J. and Xie, Y. K., (Pain 1988; 33: p 87-107).

<Methods>

Male SD rats (Charles River Japan) aged 6 weeks (n=4, each treatment performed twice in total) were used for this experiment. The rat chronic constriction injury (CCI) model was prepared in accordance with the method of Bennett and Xie above.

The common sciatic nerve was exposed at the level of the middle of the thigh by blunt dissection through biceps femoris under isoflurane anesthesia. Four ligatures (4-0 silk) were tied loosely around the sciatic nerve at about 1 mm spacing. The biceps femoris and the skin were sutured.

On 14 days after surgery, efficacy of the compounds on tactile allodynia was evaluated. The animals were housed in wire mesh bottom cages for 30 minutes prior to the start of the experiment for acclimation. The test compound was suspended in an aqueous solution containing 0.45% methyl cellulose/4.5% Cremophor/10% dimethyl sulfoxide to prepare a suspension having a dosing volume of 10 ml/kg and the suspension was administered orally. The above mixed solvent (vehicle) alone not containing the test compound was used as a negative control. The response threshold against mechanical stimulation was measured by the application of von Frey filaments at bending forces (0.4, 0.6, 1, 2, 4, 6, 8, and 15 g) to the plantar surface of the hind paw in accordance with Chaplan et al. (J Neuroscience Methods 1994; 53(1): p. 55-63). The von Frey filaments were pushed to the paw for 6 seconds to evaluate escape response. The 50% response threshold was determined in accordance with the up-down method of Dixon (Annual Review of Pharmacology and Toxicology 1980; 20: p. 441-462). The measurement was performed before administration and at 30, 90 and 180 minutes after administration. All data are expressed as the mean±SEM. All statistical analyses were performed using Two way Repeated Measures ANOVA followed by Dunnett's test. The p-values less than 0.05 were judged as statistically significant in this experiment.

<Results>

The results of tactile allodynia in CCI model are shown in Tables 7, 8, 9 and 10. Test Compounds 1 and 2 exhibited a statistically significant analgesic effect at 50 mg/kg.

TABLE 7

50% Response Threshold in von Frey Filament Test

| Treatment | 50% Response threshold (g) | | | |
|---|---|---|---|---|
| | Pre | 30 min | 90 min | 180 min |
| Vehicle | 2.5 ± 0.1 | 2.4 ± 0.2 | 2.6 ± 0.2 | 2.7 ± 0.1 |
| Compound 1 10 mg/kg | 2.4 ± 0.2 | 3.2 ± 0.3 | 4.4 ± 0.5 | 3.1 ± 0.3 |
| Compound 1 50 mg/kg | 2.3 ± 0.2 | 6.0 ± 0.7** | 11.4 ± 1.4** | 5.3 ± 0.6** |

**P < 0.01 vs vehicle (Dunnett-test)

TABLE 8

50% Response Threshold in von Frey Filament Test

| Treatment | 50% Response threshold (g) | | | |
|---|---|---|---|---|
| | Pre | 30 min | 90 min | 180 min |
| Vehicle | 2.3 ± 0.3 | 2.3 ± 0.2 | 2.3 ± 0.2 | 2.2 ± 0.2 |
| Compound 2 10 mg/kg | 2.4 ± 0.2 | 3.2 ± 0.4 | 4.1 ± 0.5 | 3.1 ± 0.2 |
| Compound 2 50 mg/kg | 2.3 ± 0.2 | 4.2 ± 0.6** | 7.6 ± 1.1** | 4.0 ± 0.5** |

**P < 0.01 vs vehicle (Dunnett-test)

TABLE 9

50% Response Threshold in von Frey Filament Test

| Treatment | 50% Response threshold (g) | | | |
|---|---|---|---|---|
| | Pre | 30 min | 90 min | 180 min |
| Vehicle | 2.4 ± 0.1 | 2.0 ± 0.2 | 3.5 ± 0.6 | 2.9 ± 0.2 |
| Compound 3 10 mg/kg | 2.4 ± 0.2 | 2.6 ± 0.4 | 3.5 ± 0.7 | 3.9 ± 0.4 |
| Compound 3 50 mg/kg | 2.4 ± 0.2 | 3.1 ± 0.4 | 3.2 ± 0.5 | 4.0 ± 0.4 |
| Compound 4 10 mg/kg | 2.4 ± 0.2 | 3.6 ± 0.4 | 5.2 ± 1.5 | 5.2 ± 1.0 |
| Compound 4 50 mg/kg | 2.4 ± 0.2 | 4.3 ± 0.9 | 6.9 ± 1.5 | 5.6 ± 1.6 |

TABLE 10

50% Response Threshold in von Frey Filament Test

| Treatment | 50% Response threshold (g) | | | |
|---|---|---|---|---|
| | Pre | 30 min | 90 min | 180 min |
| Vehicle | 2.6 ± 0.2 | 2.5 ± 0.1 | 2.7 ± 0.1 | 2.7 ± 0.2 |
| Reference Compound 1 10 mg/kg | 2.5 ± 0.2 | 2.7 ± 0.4 | 3.4 ± 0.2 | 3.4 ± 0.3 |
| Reference Compound 1 50 mg/kg | 2.5 ± 0.2 | 3.5 ± 0.3 | 3.9 ± 0.3** | 2.8 ± 0.2 |
| Reference Compound 2 10 mg/kg | 2.6 ± 0.2 | 2.9 ± 0.4 | 3.2 ± 0.4 | 3.0 ± 0.2 |
| Reference Compound 2 50 mg/kg | 2.6 ± 0.2 | 3.5 ± 0.3* | 4.5 ± 0.4** | 3.6 ± 0.6 |

*P < 0.05,
**P < 0.01 vs vehicle (Dunnett-test)

As shown in Tables 7 and 8, the response threshold against mechanical stimulation was increased in an approximately dose dependent manner by pre-administration of Test Compounds 1 and 2.

These results show an analgesic effect of the test compounds on the animal model of chronic pain.

Test Example 3

Formalin Test

The compounds were examined in the second phase of the formalin test to determine an analgesic effect on acute persistent pain. In this model, the duration of responses induced by pain (behavior such as licking or biting of the formalin-injected paw) is used as an evaluation index (Dubuisson and Dennis (Pain, 4: p. 161-174 (1977)).

<Methods>

Male CD1 (ICR) mice (Charles River Japan) aged 5 to 6 weeks (n=6 to 16, for each treatment) were used for the experiment. The responses induced by pain were measured by an automated behavioral analysis apparatus (MicroAct (Neuroscience, Inc.)) according to detection of changes in magnetic field. Before the day prior to evaluation of pain response, a small magnet for the detection of changes in magnetic field was implanted in the left hindlimb instep under isoflurane anesthesia.

For oral administration, the test compound was suspended in a solution containing 0.45% methyl cellulose/4.5% Ceremophor/10% dimethyl sulfoxide to prepare a suspension having a dosing volume of 10 ml/kg and the suspension was administered orally. The mixed solvent as above (vehicle) alone not containing the test compound was used as a negative control. Gabapentin was intraperitoneally administered as a positive control. A 2.5% formalin solution was prepared by diluting Formaldehyde Solution (Wako Pure Chemical Industries) with physiological saline (Otsuka Pharmaceutical). At 40 minutes to an hour after administration of the test compound or the positive control, 10 μl of the 2.5% formalin solution was subcutaneously injected in the left hindlimb pad. The mouse was placed in an observation chamber immediately after administration for measurement.

For evaluation of an analgesic effect in the second phase, the duration of behaviors such as licking or biting of the paw was measured by the automated behavioral analysis apparatus from 15 to 45 minutes after injection of the 2.5% formalin solution.

All data are expressed as the mean±SEM. All statistical analyses were performed using the Holm-Sidak's multiple comparisons test. The p-values less than 0.05 were judged as statistically significant in this experiment.

<Results>

Figure 2:
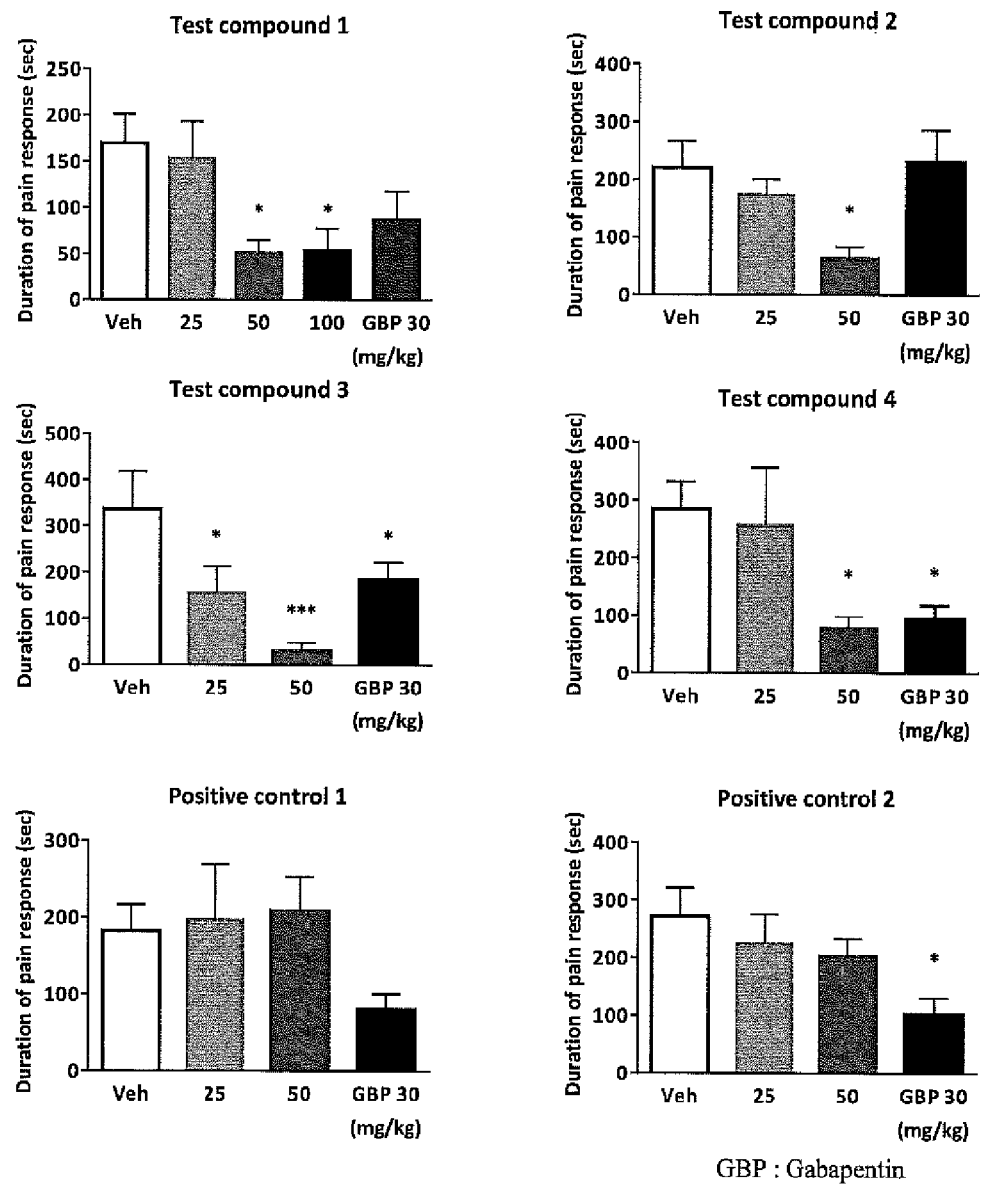
FIG. 2 is a graph showing the results of Test Example 3 in which Test Compounds 1, 2, 3 and 4 are administered.

The results of the formalin test are shown in FIG. 2. As shown in FIG. 2, the duration of the pain response was statistically significantly shortened by pre-administration of Test Compounds 1, 2, 3 and 4. These results show an analgesic effect of the compounds in an animal model of acute persistent pain.

The invention claimed is:

1. A method of treating pain in a subject in need thereof, the method comprising administering to the subject an effective amount of a compound selected from the group consisting of (1) N-[(1S)-2,2,5,7-tetrafluoro-2,3-dihydro-1H-inden-1-yl]sulfamide, (2) (−)-N-(7-chloro-2,2,5-trifluoro-2,3-dihydro-1H-inden-1-yl)sulfamide, (3) N-[(1S)-2,2-difluoro-7-methyl-2,3-dihydro-1H-inden-1-yl]sulfamide, and (4) N-[(1S)-2,2,5-trifluoro-7-methyl-2,3-dihydro-1H-inden-1-yl]sulfamide or a pharmaceutically acceptable salt thereof.

2. The method according to claim 1, wherein the pain is acute pain or chronic pain.

3. The method according to claim 1, wherein the pain is neuropathic pain.

4. The method according to claim 1, wherein the pain is diabetic neuropathy, trigeminal neuropathy or postherpetic neuralgia.

5. The method according to claim 1, wherein the compound or pharmaceutically acceptable salt thereof is administered orally, sublingually, intranasally, rectally, intragingivally, intravenously, intramuscularly, intra-articularly, subcutaneously, inhalationally, transdermally or epidurally.

6. The method according to claim 1, wherein the compound or pharmaceutically acceptable salt thereof is administered orally, sublingually, intravenously, intramuscularly, intra-articularly, subcutaneously, transdermally or epidurally.

7. The method according to claim 2, wherein the compound or pharmaceutically acceptable salt thereof is administered orally, sublingually, intranasally, rectally, intragingivally, intravenously, intramuscularly, intra-articularly, subcutaneously, inhalationally, transdermally or epidurally.

8. The method according to claim 3, wherein the compound or pharmaceutically acceptable salt thereof is administered orally, sublingually, intranasally, rectally, intragingivally, intravenously, intramuscularly, intra-articularly, subcutaneously, inhalationally, transdermally or epidurally.

9. The method according to claim 4, wherein the compound or pharmaceutically acceptable salt thereof is administered orally, sublingually, intranasally, rectally, intragingivally, intravenously, intramuscularly, intra-articularly, subcutaneously, inhalationally, transdermally or epidurally.

10. The method according to claim 2, wherein the compound or pharmaceutically acceptable salt thereof is administered orally, sublingually, intravenously, intramuscularly, intra-articularly, subcutaneously, transdermally or epidurally.

11. The method according to claim 3, wherein the compound or pharmaceutically acceptable salt thereof is administered orally, sublingually, intravenously, intramuscularly, intra-articularly, subcutaneously, transdermally or epidurally.

12. The method according to claim 4, wherein the compound or pharmaceutically acceptable salt thereof is administered orally, sublingually, intravenously, intramuscularly, intra-articularly, subcutaneously, transdermally or epidurally.

* * * * *